United States Patent [19]

Ohno et al.

[11] 4,091,111
[45] May 23, 1978

[54] SUBSTITUTED-ACETIC ACID ESTER

[75] Inventors: Nobuo Ohno, Toyonaka; Isao Ohno, Kawanishi; Toshio Nishioka, Takarazuka; Hisami Takeda, Takarazuka; Kiyoshi Kasamatsu, Takarazuka, all of Japan

[73] Assignee: Sumitomo Chemical Company Limited, Osaka, Japan

[21] Appl. No.: 728,840

[22] Filed: Oct. 1, 1976

[30] Foreign Application Priority Data

Oct. 21, 1975  Japan .................. 50-127168

[51] Int. Cl.$^2$ .................. C07C 69/76; A01N 9/24
[52] U.S. Cl. .................. 424/308; 260/330.5; 260/332.2 A; 260/332.2 C; 260/340.5 R; 260/346.22; 260/347.2; 260/347.4; 260/465 D; 424/282; 424/304; 424/309; 424/285; 424/275; 560/8; 560/9; 560/20; 560/21; 560/22; 560/23; 560/51; 560/52; 560/53; 560/54; 560/55; 560/57; 560/81; 560/100; 560/101; 560/104; 560/105

[58] Field of Search .................. 260/476 R, 469, 476; 424/308, 309; 560/100, 101, 104, 105, 8, 51, 20, 21, 22, 23, 57, 55

[56] References Cited

U.S. PATENT DOCUMENTS 4,016,179  4/1977  Fujimoto et al. .................. 260/469

Primary Examiner—Jane S. Myers
Attorney, Agent, or Firm—Farrell R. Werbow

[57] ABSTRACT

A novel substituted-arylacetic acid ester of the formula,

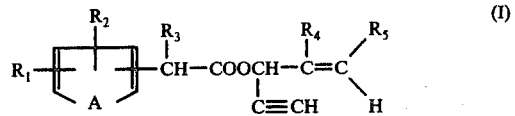

wherein $R_1$ and $R_2$ are each hydrogen or a halogen atom, a $C_1$-$C_4$ alkyl, $C_2$-$C_4$ alkenyl, $C_1$-$C_4$ alkoxy, cyano, nitro, methylthio, $C_1$-$C_4$ alkanoyl, $C_1$-$C_4$ alkanoyloxy, or $C_1$-$C_4$ alkoxycarbonyl group, or $R_1$ and $R_2$, taken together, may form methylenedioxy, a $C_3$-$C_5$ alkylene or butadienylene (—CH=CH—CH=CH—) ring; $R_3$ is a $C_2$-$C_4$ alkyl, $C_2$-$C_4$ alkenyl, propargyl, $C_3$-$C_6$ cycloalkyl or cyclopropylmethyl group; $R_4$ is hydrogen or a halogen atom, methyl or ethyl group; $R_5$ is allyl, propargyl, 3-butenyl, 3-butynyl, phenyl or benzyl group; and A is oxygen or sulfur atom or —CH=CH— group, which possesses various useful insecticidal and acaricidal activities and can be prepared by reacting a substituted-arylacetic acid of the formula;

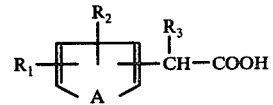

wherein $R_1$, $R_2$, $R_3$ and A are each as defined above, or a reactive derivative thereof with an alcohol, or halide or sulfonate thereof of the formula,

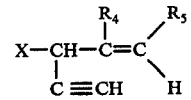

wherein $R_4$ and $R_5$ are each as defined above and X is hydroxy group, a halogen atom, alkylsulfonyloxy or arylsulfonyloxy group.

10 Claims, No Drawings

SUBSTITUTED-ACETIC ACID ESTER

The present invention relates to a novel substituted-arylacetic acid ester of the formula (I),

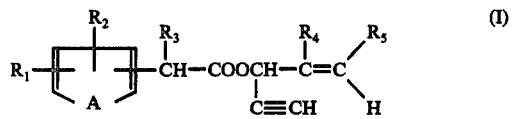

wherein $R_1$ and $R_2$ are each hydrogen or a halogen atom (preferably fluorine, chlorine or bromine atom), a $C_1$–$C_4$ alkyl, $C_2$–$C_4$ alkenyl (preferably vinyl), $C_1$–$C_4$ alkoxy (preferably $C_1$–$C_3$ alkoxy), cyano, nitro, methylthio, $C_1$–$C_4$ alkanoyl (preferably acetyl), $C_1$–$C_4$ alkanoyloxy (preferably acetyloxy) or $C_1$–$C_4$ alkoxycarbonyl (preferably methoxycarbonyl), or $R_1$ and $R_2$, taken together, may form methylenedioxy, a $C_3$–$C_5$ alkylene (preferably tri- or tetra-methylene) or butadienylene (—CH=CH—CH=CH—) ring; $R_3$ is a $C_2$–$C_4$ alkyl, $C_2$–$C_4$ alkenyl (preferably allyl), propargyl, $C_3$–$C_6$ cycloalkyl or cyclopropylmethyl group; $R_4$ is hydrogen or a halogen atom (preferably chlorine), methyl or ethyl group; $R_5$ is allyl, propargyl, 3-butenyl, 3-butynyl, phenyl or benzyl group; and A is oxygen or sulfur atom or —CH=CH— group, which possesses various useful insecticidal and acaricidal activities, and also relates to a method for the preparation thereof.

The inventors searched for a novel compound having an insecticidal activity apart from the existing insecticidally active compounds such as organo-phosphorus compounds, carbamate compounds, pyrethroidal ester groups, organo-chlorine compounds and the like. As the results, it was found that substituted acetic acid esters of aliphatic or aromatic alcohols had a wide range of insecticidal activity. Further, it was found that the alcohol moeity of the ester groups which were conventionally well known as a pyrethroidal insecticide and a substituted acetic acid provided an ester having both an activity similar to that of the conventional pyrethroid and a wider range of insecticidal spectrum [British Patent Publication No. 1439615].

Further, the inventors searched in more detail for many homologues of the ester compound and investigated their insecticidal activity and use. As the results, it was found that the present esters of the formula (I) were characteristically superior in insecticidal effect, persistency and particularly rapid effect.

The compounds of the present invention have one asymmetric carbon atom in each of the acid moeity and alcohol moeity and therefore the optical isomers thereof are also present. Among the combinations of the both isomeric moeities, the most preferred combination produces an insecticidal activity of 2 to 6 times as strong as that of the racemate.

The compounds of the present invention contain, of course, optical isomers in addition to racemates.

The novel substituted-arylacetic acid esters of the formula (I) can be obtained by reacting a substituted-arylacetic acid of the formula (II),

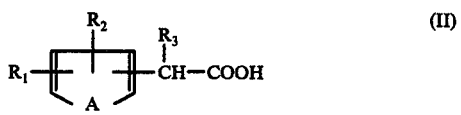

wherein $R_1$, $R_2$ and $R_3$ are as defined above, or its reactive derivative, with an alcohol halide or sulfonate of the formula (III),

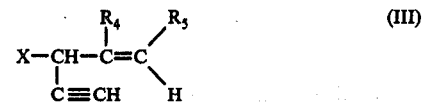

wherein $R_4$, $R_5$ and X is hydroxy group, a halogen atom, alkylsulfonyloxy or arylsulfonyloxy group.

The reactive derivatives of acid referred to herein include acid halide, acid anhydride and alkali metal salt, silver salt and organic tertiary amine salt thereof and the like.

Methods for the preparation of the present substituted-arylacetic acid esters of the formula (I) will be illustrated in more detail below.

The reaction between the acid and the alcohol is achieved by reacting the both under suitable dehydration conditions, for example, at room temperature or under heating in a suitable inert solvent such as benzene, toluene or petroleum ether in the presence of a dehydrating agent such as dicyclohexylcarbodiimide.

When an acid halide is used, the present ester is sufficiently obtained at room temperature in a high yield by reacting the acid halide with the alcohol using organic tertiary amines such as pyridine and triethylamine as a dehydrohalogenating agent. The acid halide used may optionally be selected within a range of the present invention, but an acid chloride is usually preferred. In this reaction, the presence of solvent is not essential, but it is desirable for the smooth progress of the reaction and an inert solvent such as benzene, toluene, petroleum benzine or the like is usually used.

Alternatively, when an acid anhydride is used, the reaction can be achieved by reacting the acid anhydride with the alcohol at room temperature without particular reaction assistant. In this case, heating of the reaction system and the use of an inert solvent such as toluene or xylene are desirable for the smooth progress of the reaction, but they are not essential. When the corresponding halide or sulfonate of the alcohol is used, the acid is used in the form of alkali metal salts, silver salts or organic tertiary amine salts thereof. In this case, the acid and base may be added to the reaction system at the same time so that the salt described above is produced in situ. In this case, it is desirable for performance of the reaction to use an inert solvent such as benzene, acetone, dimethylformamide or the like at the boiling point of the solvent used or at a lower temperature. As the halogen atom, a chlorine or bromine atom is frequently used.

A method for the preparation of the present compounds will be illustrated in more detail with reference to the following examples.

EXAMPLE 1

Preparation of 4-methylocta-4-ene-1,7-diyne-3-yl α-isopropyl-4-chlorophenylacetate (1)

1.40 Grams (11.4 millimoles) of 4-methylocta-4-ene-1,7-diyne-3-ol is dissolved in 20 ml of a dry benzene, followed by cooling in ice water. Thereafter, 1.80 g (22.8 millimoles) of pyridine is rapidly added thereto at a time and immediately a solution of 2.64 g (11.4 millimoles) of α-isopropyl-4-chlorophenylacetyl chloride in 10 ml of dry benzene is dropwise added thereto for about 30 minutes with stirring. After completion of the addition, stirring is continued for 3 hours at room temperature to complete the reaction. The reaction mixture is poured into 20 g of ice water and the layers are separated. The aqueous layer is extracted with two 10-ml portions of ether. The organic layers obtained is combined and washed once with a 10% hydrochloric acid and three times with water, followed by drying over anhydrous sodium sulfate. After the solvent is removed under reduced pressure, the oily substance obtained is mixed with almost the same amount of pyridine. The mixture is adsorbed to 100 g of silica gel column and purified by developing with a mixed solvent (18 : 1 : 1) of carbon tetrachloride : n-hexane : ether. Thus, 3.19 g of the objective ester is obtained as a pale yellow oily substance (85.1% of theoretical yield). $n_D^{23.0}$ 1.5233

EXAMPLE 2

Synthesis of 4-methylocta-4-ene-1,7-diyne-3-yl α-isopropyl-3,4-dichlorophenylacetate (2)

By the same procedure as in Example 1, 1.22 g (10.0 millimoles) of 4-methylocta-4-ene-1,7-diyne-3-ol, 2.66 g (10.0 millimoles) of α-isopropyl-3,4-dichlorophenylacetyl chloride and 1.58 g (20.0 millimoles) of pyridine are reacted, followed by purification on silica gel column. Thus, 3.18 g of the objective ester is obtained as a pale yellow oily substance (87.5% of theoretical yield). $n_D^{24.0}$ 1.5314

EXAMPLE 3

Synthesis of 4-methylocta-4-ene-1,7-diyne-3-yl α-isopropyl-3,4-tetramethylenephenylacetate (5)

11.61 g (50 millimoles) of α-isopropyl-3,4-tetramethylenephenylacetic acid and 6.11 g (50 millimoles) of 4-methylocta-4-ene-1,7-diyne-3-ol are dissolved in 100 ml of a dry benzene. Thereafter, 16.51 g (80 millimoles) of dicyclohexyl carbodiimide is added thereto and the resulting mixture is allowed to stand overnight in a tightly sealed flask. Next day, the reaction mixture is heated under reflux for 4 hours to complete the reaction. After cooling, the precipitated dicyclohexyl urea is filtered off.

The filtrate is concentrated and the viscous oily substance obtained is adsorbed, together with almost the same amount of pyridine, to 350 g of silica gel column and developed by passing through a mixture of chloroform : n-hexane (12 : 1) as a developing solvent. Thus, 10.63 g of the objective ester is obtained as a pale yellow oily substance (61.0% of theoretical yield). $n_D^{23.5}$ 1.5196

EXAMPLE 4

Synthesis of 6-phenyl-4-methylhexa-4-ene-1-yne-3-yl α-isopropyl-4-fluorophenylacetate (12)

7.11 Grams (20 millimoles) of α-isopropyl-4-fluorophenylacetic anhydride and 1.86 g (10 millimoles) of 6-phenyl-4-methylhexa-4-ene-1-yne-3-ol are dissolved in 30 ml of a dry pyridine. The resulting solution is stirred overnight at room temperature. Next day, the reaction solution is poured into 100 g of ice water and extracted with three 30-ml portions of ether. The ether layers obtained are combined and extracted twice with an aqueous saturated sodium hydrogen carbonate. Thereafter, the ether layer is further washed once with a 10% aqueous hydrochloric acid and three times with water, followed by drying over anhydrous sodium sulfate.

After distilling off the ether under reduced pressure, the crude ester obtained is adsorbed to 120 g of silica gel column and eluted with a mixed solvent of chloroform : n-hexane (8 : 1). Thus, 2.13 g of the objective ester is obtained as a pale yellow oily substance (58.4% of theoretical yield). $n_D^{25.5}$ 1.5118

In the same manner as described above, the compounds of the following table were obtained. In the table, a, b and c in the column of esterification method have the following meanings, a: Esterification using acid chlorides b: Esterification using acid anhydrides c: Esterification using acids and dicyclohexyl carbodiimide and (C) and (F) in the column of elementary analysis mean a calculated value and found value, respectively.

| Compound No. | Formula | Name | Esterification method | Refractive index | Yield (%) | Elementary analysis C(%) | H(%) | N(%) | X(%) | S(%) |
|---|---|---|---|---|---|---|---|---|---|---|
| 1 | (structure) | 4-Methylocta-4-ene-1,7-diyne-3-yl α-isopropyl-4-chlorophenylacetate | a | $n_D^{23.0}$ 1.5233 | 85.1 | (F) 72.91<br>(C) 73.05<br>as $C_{20}H_{21}O_2Cl$ | 6.50<br>6.44 | — | 10.17(Cl)<br>10.78(Cl) | — |
| 2 | (structure) | 4-Methylocta-4-ene-1,7-diyne-3-yl α-isopropyl-3,4-dichlorophenylacetate | a | $n_D^{24.0}$ 1.5314 | 87.5 | (F) 66.20<br>(C) 66.12<br>as $C_{20}H_{20}O_2Cl_2$ | 5.59<br>5.55 | — | 20.60(Cl)<br>19.52(Cl) | — |
| 3 | (structure) | 4-Methylocta-4-ene-1,7-diyne-3-yl α-isopropyl-4-methoxyphenylacetate | b | $n_D^{24.0}$ 1.5183 | 69.7 | (F) 77.66<br>(C) 77.75<br>as $C_{21}H_{24}O_3$ | 7.54<br>7.46 | — | — | — |
| 4 | (structure) | 4-Methylocta-4-ene-1,7-diyne-3-yl α-isopropyl-3,4-methylenedioxyphenylacetate | a | $n_D^{23.5}$ 1.5273 | 86.5 | (F) 74.31<br>(C) 74.53<br>as $C_{21}H_{22}O_4$ | 6.70<br>6.55 | — | — | — |
| 5 | (structure) | 4-Methylocta-4-ene-1,7-diyne-3-yl α-isopropyl-3,4-tetramethylenephenylacetate | c | $n_D^{23.5}$ 1.5196 | 61.0 | (F) 82.88<br>(C) 82.72<br>as $C_{24}H_{28}O_2$ | 8.09<br>8.10 | — | — | — |
| 6 | (structure) | 4-Methylocta-4-ene-1,7-diyne-3-yl 2-(5-methyl-3-furyl)-isovalerate | a | $n_D^{23.5}$ 1.5233 | 88.1 | (F) 76.52<br>(C) 76.48<br>as $C_{19}H_{22}O_3$ | 7.39<br>7.43 | — | — | — |

-continued

| Compound No. | Formula | Name | Esterification method | Refractive index | Yield (%) | Elementary analysis C(%) | H(%) | N(%) | X(%) | S(%) |
|---|---|---|---|---|---|---|---|---|---|---|
| 7 | CH₃ CH₃ / CH–CH=CH–CH₂–C≡CH / CH–COOCH / C≡CH / (5-methyl-3-thienyl) | 4-Methylocta-4-ene-1,7-diyne-3-yl 2-(5-methyl-3-thienyl)-isovalerate | a | $n_D^{25.0}$ 1.5341 | 78.7 | (F) 72.44 (C) 72.57 as C₁₉H₂₂O₂S | 7.11 7.05 | — — | — — | 10.35 10.20 |
| 8 | CH₃ CH₃ / CH–CH=CH–CH₂–C≡CH / CH–COOCH / C≡CH / (5-chloro-2-thienyl) | 4-Methylocta-4-ene-1,7-diyne-3-yl 2-(5-chloro-2-thienyl)-isovalerate | a | $n_D^{24.0}$ 1.5446 | 70.4 | (F) 64.49 (C) 64.56 as C₁₈H₁₉O₂SCl | 5.60 5.72 | — — | 10.33(Cl) 10.59(Cl) | 9.01 9.58 |
| 9 | CH₃ CH₃ / CH–CH=CH–CH₂–C≡CH / CH–COOCH / C≡CH / (2-furyl) | 4-Methylocta-4-ene-1,7-diyne-3-yl 2-(2-furyl)-isovalerate | a | $n_D^{23.5}$ 1.5235 | 60.7 | (F) 76.42 (C) 76.48 as C₁₈H₂₀O₃ | 7.50 7.43 | — — | — — | — — |
| 10 | CH₂CH₃ / CH–CH=CH–CH₂–C≡CH / CH–COOCH / C≡CH / (4-chlorophenyl) | 4-Ethylocta-4-ene-1,7-diyne-3-yl α-isopropyl-4-chlorophenylacetate | a | $n_D^{23.5}$ 1.5246 | 81.5 | (F) 73.61 (C) 73.56 as C₂₁H₂₃O₂Cl | 6.69 6.76 | — — | 10.66(Cl) 10.34(Cl) | — — |
| 11 | CH₃ CH₃ / CH–COOCH–C=CH–CH₂–CH₂–C≡CH / (4-bromophenyl) | 4-Methylnona-4-ene-1,8-diyne-3-yl α-isopropyl-4-bromophenylacetate | b | $n_D^{24.0}$ 1.5366 | 81.3 | (F) 65.08 (C) 65.12 as C₂₁H₂₃O₂Br | 6.01 5.98 | — — | 20.57(Br) 20.63(Br) | — — |
| 12 | CH₃ CH₃ / CH–COOCH–C=CH–CH₂–phenyl / C≡CH / (4-fluorophenyl) | 6-Phenyl-4-methylhexa-4-ene-1-yne-3-yl α-isopropyl-4-fluorophenylacetate | b | $n_D^{25.5}$ 1.5118 | 58.4 | (F) 78.98 (C) 79.09 as C₂₄H₂₅O₂F | 6.87 6.91 | — — | 5.21(F) | — — |
| 13 | CH₃ CH₃ / CH–COOCH–C=CH–CH₂–CH=CH₂ / C≡CH / (4-chlorophenyl) | 4-Methylocta-4,7-diene-1-yne-3-yl α-isopropyl-4-chlorophenylacetate | a | $n_D^{24.0}$ 1.5277 | 90.6 | (F) 72.93 (C) 72.60 as C₂₀H₂₃O₂Cl | 6.42 7.01 | — — | 10.81(Cl) 10.72(Cl) | — — |

-continued

| Compound No. | Formula | Name | Esterification method | Refractive index | Yield (%) | Elementary analysis C(%) | H(%) | N(%) | X(%) | S(%) |
|---|---|---|---|---|---|---|---|---|---|---|
| 14 | (structure) | 4-Methylnona-4,8-diene-1-yne-3-yl α-isopropyl-4-methoxyphenylacetate | a | $n_D^{23.8}$ 1.5206 | 88.7 | (F) 77.58 (C) 77.61 as $C_{22}H_{28}O_3$ | 8.30 8.29 | — — | — — | — — |
| 15 | (structure) | 1-Phenyl-2-methylpenta-1-ene-4-yne-3-yl α-isopropyl-4-fluorophenylacetate | a | $n_D^{24.0}$ 1.5479 | 89.3 | (F) 78.80 (C) 78.83 as $C_{23}H_{23}O_2F$ | 6.55 6.62 | — — | 5.42(F) | — — |
| 16 | (structure) | 4-Chloro-6-phenylhexa-4-ene-1-yne-3-yl α-ethyl-4-bromophenylacetate | a | $n_D^{24.5}$ 1.5644 | 87.6 | (F) 61.41 (C) 61.20 as $C_{22}H_{20}O_2ClBr$ | 4.54 4.67 | — — | — — | — — |
| 17 | (structure) | 4-Methylocta-4-ene-1,7-diyne-3-yl α-cyclopropyl-4-methylphenylacetate | a | $n_D^{26.0}$ 1.5517 | 86.2 | (F) 82.40 (C) 82.32 as $C_{21}H_{22}O_2$ | 7.36 7.42 | — — | — — | — — |
| 18 | (structure) | 4-Methylocta-4-ene-1,7-diyne-3-yl α-isopropyl-3-methoxycarbonylphenylacetate | a | $n_D^{25.5}$ 1.5228 | 45.6 | (F) 74.89 (C) 74.97 as $C_{22}H_{24}O_4$ | 6.92 6.86 | — — | — — | — — |
| 19 | (structure) | 4-Methylocta-4-ene-1,7-diyne-3-yl α-t-butyl-3,4-dimethoxyphenylacetate | a | $n_D^{23.0}$ 1.5367 | 81.5 | (F) 75.10 (C) 74.97 as $C_{23}H_{28}O_4$ | 7.58 7.66 | — — | — — | — — |
| 20 | (structure) | 4-Methylocta-4-ene-1,7-diyne-3-yl α-allyl-4-isopropoxyphenylacetate | a | $n_D^{23.0}$ 1.5422 | 66.6 | (F) 78.80 (C) 78.82 as $C_{23}H_{26}O_3$ | 7.50 7.48 | — — | — — | — — |

-continued

| Compound No. | Formula | Name | Esterification method | Refractive index | Yield (%) | Elementary analysis | | | | |
|---|---|---|---|---|---|---|---|---|---|---|
| | | | | | | C(%) | H(%) | N(%) | X(%) | S(%) |
| 21 | CH₃ CH₃ CH-CH₃ CH-COOCH-C=CH-CH₂-C≡CH C≡CH (4-t-butylphenyl) | 4-Methylocta-4-ene-1,7-diyne-3-yl α-isopropyl-4-t-butylphenylacetate | c | $n_D^{24.5}$ 1.5442 | 59.4 | (F) 82.17 (C) 82.24 as C₂₄H₃₀O₂ | 8.74 8.63 | — — | — — | — — |
| 22 | CH₃ (cyclohexyl)-CH-COOCH-C=CH-CH₂-C=CH₂ C≡CH | 4-Methylocta-4,7-diene-1-yne-3-yl α-cyclohexylphenylacetate | a | $n_D^{23.0}$ 1.5122 | 85.4 | (F) 82.16 (C) 82.10 as C₂₃H₂₈O₂ | 8.46 8.39 | — — | — — | — — |
| 23 | CH₂CH₃ CH₃ NC-C₆H₄-CH-COOCH-C=CH-CH₂-C≡CH C≡CH | 4-Methylnona-4-ene-1,8-diyne-3-yl α-ethyl-4-cyanophenylacetate | a | $n_D^{25.0}$ 1.5225 | 57.4 | (F) 79.02 (C) 78.97 as C₂₁H₂₁O₂N | 6.55 6.63 | 4.29 4.39 | — — | — — |
| 24 | CH₃ CH-CH₃ Cl-C₆H₄-CH-COOCH-C=CH-CH₂-C≡CH C≡CH | Octa-4-ene-1,7-diyne-3-yl α-isopropyl-4-chlorophenylacetate | b | $n_D^{25.0}$ 1.5247 | 60.8 | (F) 72.46 (C) 72.49 as C₁₉H₁₉O₂Cl | 6.01 6.08 | — — | 11.35(Cl) 11.26(Cl) | — — |
| 25 | CH₂CH₃ CH₂C≡CH CH₃CH₂-C₆H₄-CH-COOCH-C=CH-CH₂-CH=CH₂ | 4-Ethylnona-4,8-diene-1-yne-3-yl α-propargyl-4-ethylphenylacetate | a | $n_D^{25.0}$ 1.5417 | 89.5 | (F) 82.66 (C) 82.72 as C₂₄H₂₈O₂ | 8.08 8.10 | — — | — — | — — |
| 26 | CH₂ CH₂ CH₃ CH₂-CH CH₂-CH CH₃CH₂O-C₆H₄-CH-COOCH-C=CH-CH₂-C≡CH C≡CH | 4-Methylocta-4-ene-1,7-diyne-3-yl α-cyclopropylmethyl-4-ethoxyphenylacetate | a | $n_D^{27.5}$ 1.5298 | 87.7 | (F) 78.76 (C) 78.82 as C₂₃H₂₈O₃ | 7.52 7.48 | — — | — — | — — |

-continued

| Compound No. | Formula | Name | Esterification method | Refractive index | Yield (%) | Elementary analysis C(%) H(%) N(%) X(%) S(%) |
|---|---|---|---|---|---|---|
| 27 | [structure with CH₃-S-C₆H₄-CH(CH(CH₃)₂)-COOCH(C≡CH)-CH=CH-C₆H₅] | 5-Phenylpenta-4-ene-1-yne-3-yl α-isopropyl-4-methylthiophenylacetate | b | $n_D^{25.0}$ 1.5471 | 60.1 | (F) 75.33 6.70 — — 8.84<br>(C) 75.29 6.64 — — 8.79<br>as $C_{23}H_{24}O_2S$ |
| 28 | [structure with NO₂-C₆H₄-CH(CH₂CH₂CH₃)-COOCH-C(CH₃)=CH-CH₂-CH=CH₂ with C≡CH] | 4-Methylocta-4,7-diene-1-yne-3-yl α-propyl-4-nitrophenylacetate | a | $n_D^{24.5}$ 1.5544 | 61.6 | (F) 70.33 6.82 4.30 — —<br>(C) 70.36 6.79 4.10 — —<br>as $C_{20}H_{23}O_4N$ |
| 29 | [tetrahydrobenzothienyl structure with isovalerate] | 4-Methylocta-4-ene-1,7-diyne-5-yl 2-(4,5,6,7-tetrahydro-2-benzothienyl)-isovalerate | a | $n_D^{23.0}$ 1.5629 | 79.5 | (F) 74.48 7.41 — — 8.92<br>(C) 74.53 7.39 — — 9.05<br>as $C_{22}H_{26}O_2S$ |
| 30 | [4,5-trimethylene-thienyl structure with isovalerate] | 4-Methylocta-4-ene-1,7-diyne-3-yl 2-(4,5-trimethylene-thienyl)-isovalerate | a | $n_D^{24.5}$ 1.5576 | 73.7 | (F) 74.16 7.18 — — 9.60<br>(C) 74.08 7.10 — — 9.42<br>as $C_{21}H_{24}O_2S$ |
| 31 | [2-benzothienyl structure with isovalerate] | 4-Methylocta-4-ene-1,7-diyne-3-yl 2-(2-benzothienyl)-isovalerate | a | $n_D^{26.0}$ 1.5735 | 83.4 | (F) 75.37 6.42 — — 9.02<br>(C) 75.39 6.33 — — 9.15<br>as $C_{22}H_{22}O_2S$ |
| 32 | [3-benzothienyl structure with isovalerate] | 4-Methylocta-4-ene-1,7-diyne-3-yl 2-(3-benzothienyl)-isovalerate | a | $n_D^{24.0}$ 1.5699 | 80.9 | (F) 75.30 6.37 — — 9.20<br>(C) 75.39 6.33 — — 9.15<br>as $C_{22}H_{22}O_2S$ |

-continued

| Compound No. | Formula | Name | Esterification method | Refractive index | Yield (%) | Elementary analysis C(%) | H(%) | N(%) | X(%) | S(%) |
|---|---|---|---|---|---|---|---|---|---|---|
| 33 | CH₃-CH(CH₃)-CH(-COOCH-C=CH-CH₂-C≡CH)(C≡CH), attached to 5-indanyl | 4-Methylocta-4-ene-1,7-diyne-3-yl 2-(5-indanyl)-isovalerate | a | $n_D^{23.5}$ 1.5427 | 85.9 | (F) 82.66 (C) 82.59 as C₂₃H₂₆O₂ | 7.99 7.84 | — — | — — | — — |
| 34 | (2-benzofuryl) variant | 4-Methylocta-4-ene-1,7-diyne-3-yl 2-(2-benzofuryl)-isovalerate | a | $n_D^{25.0}$ 1.5366 | 64.3 | (F) 79.00 (C) 79.01 as C₂₂H₂₂O₃ | 6.70 6.63 | — — | — — | — — |
| 35 | 4-acetylphenyl variant | 4-Methylocta-4-ene-1,7-diyne-3-yl α-isopropyl-4-acetylphenylacetate | a | $n_D^{25.0}$ 1.5318 | 77.6 | (F) 78.62 (C) 78.54 as C₂₂H₂₄O₃ | 7.24 7.19 | — — | — — | — — |
| 36 | 3-vinylphenyl variant | 4-Methylocta-4-ene-1,7-diyne-3-yl α-isopropyl-3-vinylphenylacetate | a | $n_D^{26.5}$ 1.5633 | 70.0 | (F) 82.51 (C) 82.46 as C₂₂H₂₄O₂ | 7.54 7.55 | — — | — — | — — |
| 37 | 4-acetylphenyl, chloro-hexaene-yne | 4-Chloro-6-phenylhexa-4-ene-1-yne-3-yl α-isopropyl-4-acetyloxyphenylacetate | a | $n_D^{24.0}$ 1.5416 | 67.8 | (V) 70.49 (C) 70.66 as C₂₅H₂₅O₄Cl | 6.02 5.93 | — — | 8.41(Cl) 8.34(C) | — — |
| 38 | 3,4-methylenedioxyphenyl variant | 4-Methylnona-4,8-diene-1-yne-3-yl α-isopropyl-3,4-methylenedioxyphenylacetate | a | $n_D^{25.0}$ 1.5288 | 88.1 | (F) 74.52 (C) 74.55 as C₂₂H₂₆O₄ | 7.31 7.39 | — — | — — | — — |

The substituted-arylacetic acid esters of the present invention which are represented by the formula (I) have both a rapid effect and an excellent insecticidal activity. Further, the esters are expected to exhibit a repelling effect on mites and a synergistic effect together with other compounds having a biological activity. Still further, the esters are widely used as compositions for controlling insects injurious to agriculture, horticulture, forestry, sanitation and stored cereals and mites, and are available at low cost.

In the practical application of these compounds, they may be applied alone or in combination with suitable amounts of one or more of solvent, filler, diluent, active agent, dispersing agent, surface active agent, wetting agent, pressure-applying agent, emulsifying agent and attractant and used in the form of emulsifiable concentrates, wettable powders, dusts, granules, fine granules, powdered granules, coatings, oil sprays, aerosols, mosquito coils, fumigants, heating fumigants, electric mosquito killers, baits and the like.

The excellent effects of the present compounds will become more apparent by the following experimental examples.

Experimental Example 1

An emulsifiable concentrate is prepared by blending 30% of each of the present compounds (1) to (35), 50% of xylene and 20% of Sorpol SM-200 (a registered trade mark of Toho Kagaku Co.).

The emulsifiable concentrates thus formulated were diluted 300 times with water. In the same manner, commercially available 30% wettable powder, Carbaryl (1-naphthyl-N-methylcarbamate) was diluted as a control. Each test solution thus prepared was individually sprayed on the rice plants in a pot which had elasped 25 days after sowing, in a proportion of 10 ml/pot. Thereafter, each pot was covered with a cylindrical wire net and 15 green rice leafhoppers (*Nephotettix cincticeps*) were liberated in the pot. After one day, the death and alive were observed and as the result, a mortality of more than 90% was obtained with a every present compound and Carbaryl.

Experimental Example 2

An emulsifiable concentrate is prepared by blending 20 parts of each of the following present compounds, 60 parts of xylene and 20 parts of Sorpol SM-200 (a registered trade mark of Toho Kagaku Co.). The following compounds as a control are also treated in the same manner as described above.

The emulsifiable concentrates thus formulated were diluted with water to a required concentration. Each test solution thus prepared was individually sprayed on the rice plants in a pot which had elapsed 25 days after sowing, in a proportion of 10 ml/pot. Thereafter, each pot was covered with a cylindrical wire net and 15 smaller brown planthoppers (*Laodelphax striatellus*) were liberated in the pot. After one day, the death and alive were observed and the value of $LC_{50}$ of every concentrate was obtained from the mortality.

The compounds of the present invention are expressed by the foregoing compound number. The experimental results are shown in the following table.

| Test compound | | $LC_{50}$ (PPM) |
|---|---|---|
| Present compound | (1) | 23 |
| " | (2) | 31 |
| " | (3) | 35 |
| " | (4) | 28 |
| " | (6) | 32 |
| " | (10) | 34 |
| " | (14) | 46 |
| " | (19) | 43 |
| " | (23) | 50 |
| " | (27) | 66 |
| " | (29) | 48 |
| " | (32) | 50 |
| 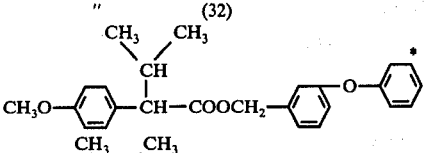 | | 87 |
| 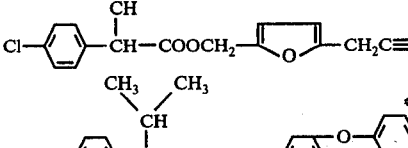 | | 68 |
| 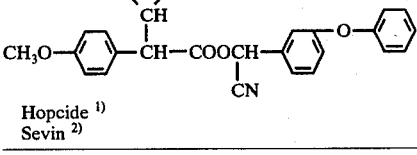 | | 73 |
| Hopcide [1] | | 75 |
| Sevin [2] | | 193 |

[1] 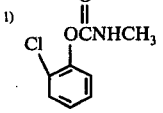

[2] 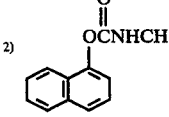

*The compound disclosed in British Patent Publication No. 1439615

Experimental Example 3

Each of the following present compounds is formulated into a 0.1% oil spray using deodorized kerosene. The following compounds as a control are also likewise treated.

About 50 house-fly adults (*Musca domestica*) are liberated in a (70 cm)³ glass chamber. Thereafter, 0.7 ml of each oil spray is sprayed under a pressure of 1.5 kg/cm² and the knock-down of the insects with the lapse of time is observed. This test is repeated several times with each oil spray to obtain the values of $KT_{50}$ (time required for 50% knock-down) as shown in the following table. The present compounds are indicated by the foregoing compound number.

| Test compound | | $KT_{50}$ (second) |
|---|---|---|
| Present compound | (1) | 128 |
| " | (3) | 139 |
| " | (4) | 136 |
| " | (5) | 140 |
| " | (7) | 175 |
| " | (11) | 147 |
| " | (14) | 174 |
| " | (23) | 140 |
| " | (30) | 158 |
| " | (34) | 170 |

-continued

| Test compound | KT$_{50}$ (second) |
|---|---|
| (structure: Cl-C6H4-CH(CH(CH3)2)-COOCH2-furan-CH2-C6H5) | 510 |
| (structure: CH3O-C6H4-CH(CH(CH3)2)-COOCH(C≡CH)-furan-CH2C≡CH*) | 183 |
| (structure: CH3O-C6H4-CH(CH(CH3)2)-COOCH(CN)-furan-O-C6H5) | 490 |
| Allethrin[3] | 504 |
| Resmethrin[4] | >600 |
| Pyrethrins | 180 |

3) CH$_2$=CH-CH$_2$- (cyclopentenyl)-O-CH-CH-CH=C(CH$_3$)$_2$ with C(CH$_3$)$_2$ 4) C$_6$H$_5$-CH$_2$-furan-CH$_2$OC(O)-CH-CH-CH=C(CH$_3$)$_2$ with C(CH$_3$)$_2$

*The compound disclosed in British Patent Publication No. 1439615

Experimental Example 4

Each of the following present compounds is formulated into a 0.2% oil spray using deodorized kerosene. The compounds as a control are also likewise treated.

Nylon net of about 15 mesh is set up at the bottom of a glass cylinder (20 cm in diameter and 20 cm in height) and butter is coated on the inside wall in a width of about 3 cm at the upper part and twenty German cockroach adults (*Blattella germanica*) are liberated therein and another same glass cylinder is then placed thereon. 0.5 Ml of each oil spray is sprayed into the glass cylinder under a pressure of 0.75 kg/cm$^2$ through a glass atomizer. After covering the cylinder, the knock-down of the insects with the lapse of time is observed. This test is repeated several times with each oil spray to obtain the values of KT$_{50}$ (time required for 50% knockdown) as shown in the following table.

The present compounds are indicated by the foregoing compound number.

| Test compound | | KT$_{50}$ (min. sec) |
|---|---|---|
| Present compound | (1) | 5'00" |
| | (2) | 6'10" |
| | (3) | 4'30" |
| | (4) | 3'50" |
| | (8) | 10'10" |
| | (13) | 9'20" |
| | (15) | 13'40" |
| | (19) | 14'00" |
| | (23) | 8'10" |
| | (29) | 12'20" |
| | (34) | 11'50" |

-continued

| Test compound | KT$_{50}$ (min. sec) |
|---|---|
| (structure: Cl-C6H4-CH(CH(CH3)2)-COOCH2-furan-CH2-C6H5*) | >20' |
| (structure: CH3O2C-furan-CH(CH(CH3)2)-COOCH2-C6H4-O-C6H5*) | >20' |
| (structure: CH3O-C6H4-CH(CH(CH3)2)-COOCH(C≡CH)-furan-CH2C≡CH*) | 15'10" |

*The compound disclosed in British Patent Publication No. 1439615

As is apparent from the aforesaid experimental results, the compounds of the present invention exhibit an excellent biological activity. When the compounds have an isomer thereof, the activity is further enhanced by resolution of the compounds into the optical isomers thereof. In this respect, the compounds of the present invention are very useful for controlling insects injurious to agriculture such as, for example, green rice leafhopper, planthoppers, rice stem borer, armyworms and cutworms, diamond-back moth, cut worm, cabbage worm, Japanese giant silk moth, tortorix, aphids, mealybug and scales and the like; insects injurious to stored cereals such as, for example, rice weevils; and mites.

In particular, the compounds of the present invention are very superior in that they can freely be used, due to their low toxicity and harmlessness to mammals, for agricultural crops before harvest, household horticulture, green-house cultivation and food-packaging.

In the preparation of the present compositions, it is also possible to develop a more superior controlling effect by the combined use of two or more compounds of the present invention. Further, it is possible to obtain multipurpose compositions having a more superior effect by blending with other insecticides and other chemicals. The insecticides include organo-chlorine type insecticides such as DDT, BHC and methoxychlor; organo-phosphorus type insecticides such as 0,0-dimethyl-0-(3-methyl-4-nitrophenyl)-phosphorothioate [hereinafter referred to as Sumithion (a registered trade mark of Sumitomo Chemical Co.)], Diazinon, Fenthion, 0,0-dimethyl-0-4-cyanophenyl-phosphorothioate [hereinafter referred to as Cyanox (a registered trade mark of Sumitomo Chemical Co.)], 0,0-dimethyl-S-[α-(ethoxycarbonyl)benzyl]-phosphorodithioate [hereinafter referred to as Papthion (a registered trade mark of Bayer Co.)], 2-methoxy-4H-1,3,2-benzodioxaphosphorin-2-sulfide [hereinafter referred to as Salithion (a registered trade mark of Sumitomo Chemical Co.)], and 0-ethyl-0-4-cyanophenylphenylphosphonothioate [hereinafter referred to as Surecide (a registered trade mark of Sumitomo Chemical Co.)]; carbamate type insecticides such as 1-naphthyl-4-methylcarbamate, 3,4-dimethylphenyl-N-methylcarbamate, 3,5-dimethylphenyl-N-methylcarbamate and 2-isopropoxyphenyl-N-methylcarbamate; pyrethrin, allethrin, N-(3,4,5,6-tetrahydrophthalimido)-methyl chrysanthemate [hereinafter referred to as Neo-pynamin (a registered trade mark of Sumitomo Chemical Co.)], 5-benzyl-3-furylmethyl chrysanthemate [hereinafter referred to as Crysron (a registered trade mark of Sumitomo Chemical Co.)], 5-propargylfurfurylmethyl chrysanthemate, 5-propargyl-2-methyl-3-furylmethyl chrysanthemate, 3-phenoxybenzyl chrysanthemate, the geometric and optical isomers thereof, the well-known cyclopropanecarboxylic esters other than those mentioned above, and the synergists for them such as piperonylbutoxide, sulfoxide, sufroxane, MGK-264, I.B.T.A. and S-421. The chemicals include the compounds used for the preparation of heating fumigants such as terephthalic acid, isophthalic acid and BHT; stabilizers such as phenol derivatives, bisphenol derivatives, arylamines (e.g. phenyl-$\beta$-naphthylamine, phenyl-$\beta$-naphthylamine and condensation products of phenetidine and acetone) and other well-known antioxidants; and other agricultural chemicals, for example, insecticides such as Padan, Galecron and Lannate, acaricides, fungicides, nematocides, herbicides, plant regulators, fertilizers and other chemicals.

By the preparation of these multipurpose compositions, it can sufficiently be expected to attain saving in labor and synergistic effects by the combined use of the chemicals.

The preparation and controlling effect of the present composition will be illustrated with reference to the following preparation examples and examples, which are not of course intended to limit the invention thereto.

Preparation Example 1

To 20 parts of each of the present compounds (1), (2), (3), (4), (5), (8), (10), (11), (14), (18), (19), (21), (23), (28), (30) and (33) are added 20 parts of Sorpol SM-200 (the same as above) and 60 parts of xylene. The mixtures are each throughly mixed to make a solution. Thus emulsifiable concentrate of each compound is obtained.

Preparation Example 2

To 15 parts of each of the present compounds (2), (4), (11), (23) and (35) are added 25 parts of natural pyrethrum extracts (pyrethrin content 20%), 20 parts of Sorpol SM-200 (the same as above) and 40 parts of xylene. The mixtures are each thoroughly mixed to make a solution. Thus emulsifiable concentrate of each compound is obtained.

Preparation Example 3

To 20 parts of each of the present compounds (1), (4), (6), (10), (11), (19), (23), (29) and (33) are added 20 parts of Cyanox (the same as above), 20 parts of Sorpol SM-200 (the same as above) and 40 parts of xylene. The mixtures are each thoroughly mixed to make a solution. Thus emulsifiable concentrate of each compound is obtained.

Preparation Example 4

To 15 parts of each of the present compounds (2), (8), (13), (20) and (32) are added 25 parts of Sumithion (the same as above), 20 parts of Sorpol SM-200 (the same as above) and 40 parts of xylene. The mixtures are each thoroughly mixed to make a solution. Thus emulsifiable concentrate of each compound is obtained.

Preparation Example 5

Fifteen parts of each of the present compounds (1) to (35), 15 parts of 1-naphthyl-N-methylcarbamate and 5 parts of Sorpol SM-200 (the same as above) are thoroughly mixed. The mixtures are each mixed with 65 parts of 300 mesh diatomaceous earth in a mortar while thoroughly stirring. Thus wettable powder of each compound is obtained.

Preparation Example 6

One part of each of the present compounds (2), (4), (5), (7), (12), (17), (20), (21), (22), (25), (26), (32) and (35) and 5 parts of piperonyl-butoxide are dissolved in 20 parts of acetone, and then 94 parts of 300 mesh talc are added thereto. After thoroughly mixing in a mortar while stirring, acetone is removed by evaporation. Thus dust of each compound is obtained.

Preparation Example 7

0.1 Part of each of the present compounds (1), (4) and (29) is dissolved in kerosene to become a total weight of 100 parts. Thus oil spray of each compound is obtained.

Preparation Example 8

0.1 part of each of the present compounds (2), (5), (8), (12), (17), (23), (29) and (35), 0.1 part of Neo-pynamin (the same as above) and 0.8 part of S-421 are dissolved in kerosene to become a total weight of 100 parts. Thus oil spray of each compound is obtained.

Preparation Example 9

0.1 Part of each of the present compounds (3), (9), (11), (15), (20), (22), (25), (30) and (34), 0.1 part of d-trans chrysanthemic ester of allethrin and 0.6 part of piperonyl-butoxide are dissolved in kerosene to become a total weight of 100 parts. Thus oil spray of each compound is obtained.

Preparation Example 10

0.2 Part of each of the present compounds (1), (4), (8) and (23), 0.2 part of 2-isopropoxyphenyl N-methylcarbamate and 5 parts of xylene are dissolved in kerosene to become a total weight of 100 parts. Thus oil spray of each compound is obtained.

Preparation Example 11

Each of the insecticidal groups comprising the active ingredients in a composition shown in the following recipes is dissolved in a mixed solvent of xylene and purified kerosene (1 : 1) to become a total weight of 15 parts. The solutions are each filled in an aerosol container. After attaching a valve portion to the container, 85 parts of a propellent (e.g. freon, vinylchloride monomer, liquefied petroleum gas) is charged therein under pressure through the valve. Thus aerosol of each compound is obtained.

| Recipe | Recipe of aerosol formulation Composition | |
|---|---|---|
| A | present compound (1) | 0.3 part |
|   | 3-phenoxybenzyl d-cis,trans chrysanthemate | 0.1 part |
| B | present compound (1) | 0.4 part |
|   | piperonyl-butoxide | 2.0 parts |
| C | present compound (2) | 0.3 part |
|   | DDVP | 0.3 part |
| D | present compound (3) | 0.2 part |
|   | d-trans chrysanthemic ester of allethrin | 0.2 part |
|   | sufroxane | 2.0 parts |
| E | present compound (4) | 0.2 part |
|   | Neo-pynamin | 0.2 part |
|   | piperonyl-butoxide | 2.0 parts |
| F | present compound (4) | 0.3 part |
|   | Neo-pynamin | 0.2 part |
|   | I.B.T.A. | 1.0 part |

-continued

| Recipe | Recipe of aerosol formulation Composition | |
|---|---|---|
| G | present compound (13) | 0.2 part |
|   | Neo-pynamin | 0.2 part |
|   | Sumithion | 0.3 part |
| H | present compound (23) | 0.2 part |
|   | Neo-pynamin | 0.2 part |
|   | Crysron | 0.1 part |
| I | present compound (28) | 0.2 part |
|   | d-cis, trans chrysanthemic ester of allethrin | 0.2 part |
|   | sufroxane | 2.0 parts |
| J | present compound (33) | 0.3 part |
|   | d-trans chrysanthemic ester of allethrin | 0.2 part |

Preparation Example 12

Each of the insecticidal groups comprising the active ingredients in a composition shown in the following recipes is dissolved in 20 ml of methanol. To each solution is added a mosquito coil carrier (containing Tabu powder, pyrethrum marc and wood powder in a ratio of 3 : 5 : 1) to become a total weight of 100 g. The mixtures are each thoroughly mixed while stirring and then the methanol is evaporated. To the residue obtained is added 150 ml of water and the mixture is kneaded thoroughly, shaped into a mosquito coil and dried. Thus mosquito coil of each compound is obtained.

| Recipe | Recipe of mosuito coil formulation Composition | |
|---|---|---|
| A | present compound (1) | 0.3 g |
|   | allethrin | 0.2 g |
|   | BHT | 0.3 g |
| B | present compound (3) | 0.3 g |
|   | d-trans chrysanthemic ester of allethrin | 0.1 g |
|   | BHT | 0.4 g |
| C | present compound (4) | 0.2 g |
|   | 5-propargylfurfuryl chrysanthemate | 0.2 g |
|   | BHT | 0.8 g |
| D | present compound (19) | 0.3 g |
|   | 5-propargyl-2-methyl-3-furylmethyl chrysanthemate | 0.1 g |
|   | BHT | 0.4 g |

Preparation Example 13

Each of the insecticidal groups comprising the active ingredients in a composition shown in the following recipes is dissolved in a suitable amount of chloroform. The solutions are each adsorbed uniformly to the surface of asbestos (2.5 cm × 1.5 cm in size and 0.3 mm in thickness), and then asbestos of the same size is struck thereon. Thus fibrous heating fumigant insecticidal composition for use on a heater of each compound is obtained. Pulp plate may be used as a fibrous carrier having the same effect in place of asbestos.

Recipe for the formulation of heating fumigant for use on a heater

| Recipe | Recipe for the formulation of heating fumigant for use on a heater Composition | |
|---|---|---|
| A | present compound (1) | 0.05 g |
|   | allethrin | 0.02 g |
|   | piperonyl-butoxide | 0.07 g |
| B | present compound (4) | 0.07 g |
|   | d-trans chrysanthemic ester of allethrin | 0.01 g |
|   | piperonyl-butoxide | 0.1 g |
| C | present compound (5) | 0.05 g |
|   | 5-propargyl-2-furylmethyl chrysanthemate | 0.02 g |
|   | piperonyl-butoxide | 0.15 g |
|   | BHT | 0.1 g |
| D | present compound (10) | 0.05 g |
|   | 5-propargyl-2-methyl-3-furylmethyl chrysanthemate | 0.02 g |
|   | piperonyl-butoxide | 0.15 g |
| E | present compound (23) | 0.04 g |
|   | allethrin | 0.04 g |
|   | piperonyl-butoxide | 0.08 g |
|   | BHT | 0.1 g |

Preparation Example 14

To 2 parts of each of the wettable powders formulated according to Preparation Example 6 is added 98 parts of corn meal and then mixed thoroughly to obtain a bait. The bait is applied as it is in a practical use.

Preparation Example 15

Five parts of each of the present compounds (1) to (35), 5 parts of sodium ligninsulfonate, 85 parts of Fubasami clay and 5 parts of water are thoroughly kneaded, granulated by means of a granulator and dried. Thus granular preparation of each compound is obtained. The granular preparation is applied as it is in a practical use.

The insecticidal effect of the thus obtained present compositions on insects injurious to cereals will be illustrated with reference to the following examples.

EXAMPLE 5

Each of the emulsifiable concentrates formulated according to Preparation Example 1 was diluted 200 times with water. Ten larvae of tabacco cut worm (*Spodoptera litura*) in the third instar stage were liberated in a glass Petri dish of 14 cm in diameter and 1 ml of each test solution thus prepared was sprayed from the spraying tower. Thereafter, the larvae were liberated in another dish in which feed had previously been placed. After two days, more than 80% of the larvae were killed with any concentrate.

EXAMPLE 6

Each of the emulsifiable concentrates formulated according to Preparation Example 2 was diluted 200 times with water. Each test solution thus prepared was sprayed on the field, in a proportion of 100 l/tan, wherein radish had been grown up to a 5- to 6-leaf stage over the whole surface and a numerous number of green peach aphids (*Myzus persicae*) had been made parasitic on the leaves of the radish. After two days, a density of parasitism was checked and it was found that the density was reduced to less than one-tenth of its initial value in every plot.

EXAMPLE 7

Each of the emulsifiable concentrates formulated according to Preparation Example 3 was diluted 200 times with water. A plywood of 15 cm × 15 cm in size was coated with each test solution thus prepared in a proportion of 50 ml/m$^2$ and air-dried. Thereafter, German cockroach adults (*Blattella germanica*) were brought into contact with the plywood for 1 hour. After three days, more than 80% of the test insects were killed with any concentrate.

EXAMPLE 8

Each of the emulsifiable concentrates formulated according to Preparation Example 4 was diluted 200 times with water. Each test solution thus prepared was sprayed on a eggplant (grown-up) field, in a proportion of 100 l/tan, on which a numerous number of 28-spotted lady bettle larvae (*Epilachna vigintioctopunctata*) were made parasitic. After 30 minutes, knock-down of the insect in every plot was checked and it was found that more than 90% of the larvae fell down to the ground. After 24 hours, the density of parasitism was checked and it was found that a control effect close to 100% was obtained in every plot in comparison with that obtained with a control plot.

EXAMPLE 9

Each of the wettable powders formulated according to Preparation Example 5 was diluted 400 times with water. Each test solution thus prepared was sprayed on the rice plants in a 1/50,000 Wagner pot which had elapsed 45 days after sowing, in a proportion of 10 ml/pot. Thereafter, each pot was covered with a cylindrical wire net and about 20 smaller brown planthopper adults (*Laodelphax striatellus*) were liberated in the pot. After one day, more than 80% of the test insects were killed with any wettable powder.

EXAMPLE 10

Each of the dusts formulated according to Preparation Example 6 was uniformly dusted on the bottom of a glass Petri dish of 14 cm in diameter, in a proportion of 2 g/m$^2$. The dish was coated on the inside wall with butter, leaving at the lower part an uncoated portion of 1 cm in width.

Thereafter, 10 German cockroach adults (*Blattella germanica*) per group were liberated in the dish and allowed to come into contact with the dust for 30 minutes. The test insects were then moved to another dish. After three days, more than 80% of the adults were killed with any dust.

EXAMPLE 11

Five milliliters of each of the oil sprays formulated according to Preparation Example 7 was sprayed, using Campbel's turn table apparatus [Soap and Sanitary Chemicals, Vol. 14, No. 6, 119 (1938)]. Twenty seconds after spraying, the shutter was opened, and about 100 house-fly adults (*Musca domestica*) per group were exposed to the descending mist for 10 minutes. The flies were then fed and allowed to stand. Next day, more than 80% of the house-fly were killed with any oil spray.

EXAMPLE 12

About 50 house-fly adults (*Musca domestica*) were liberated in a (70 cm)$^3$ glass chamber. Thereafter, 0.7 ml of each of the oil sprays formulated according to Preparation Example 8 was sprayed in the chamber under a pressure of 1.5 kg/cm$^2$. After 10 minutes, more than 80% of the flies were knocked down.

EXAMPLE 13

About 50 northern house mosquito adults (*Culex pipiens pallens*) were liberated in a (70 cm)$^3$ chamber. Thereafter, 0.7 ml of each of the oil sprays formulated according to Preparation Example 9 was sprayed in the chamber under a pressure of 1.5 kg/cm$^2$. After 10 minutes, more than 80% of the mosquitos were knocked down.

EXAMPLE 14

Nylon net of about 15 mesh was set up at the bottom of a glass cylinder (20 cm in diameter and 20 cm in height) and butter was coated on the inside wall thereof in a width of about 3 cm at the upper part. Twenty German cockroach adults (*Blattella germanica*) were liberated therein.

The glass cylinder containing the cockroaches was piled on another same glass cylinder and further a glass cylinder (20 cm in diameter and 40 cm in height) was piled on the former glass cylinder. Thereafter, 0.5 ml of each of the oil sprays formulated according to Preparation Example 10 was sprayed into the cylinder at the top thereof under a pressure of 0.75 kg/cm$^2$ through a glass atomizer. After covering the cylinder, the adults were allowed to stand. After three days, more than 90% of the test insects were killed.

EXAMPLE 15

The insecticidal activity on house-fly adults (*Musca domestica*) of the aerosols formulated according to Preparation Example 11 was tested by the aerosol test method (Soap and Chemical Specialities, Blue Book, 1965) using Peet Grady's chamber. Thus, with any aerosol, more than 80% of the flies were knocked down 15 minutes after spraying and more than 70% of the flies were killed by the next day.

EXAMPLE 16

About 50 northern house mosquito adults (*Culex pipiens pallens*) were liberated in a (70 cm)$^3$ glass chamber. One gram of each of the mosquito coils formulated according to Preparation Example 12 was ignited at the both ends and placed at the center of the bottom of the chamber. After 20 minutes, more than 80% of the mosquitos were knocked down.

EXAMPLE 17

About 50 northern house mosquito adults (*Culex pipiens pallens*) were liberated in a (70 cm)$^3$ glass chamber. Each of the heating fumigant compositions formulated according to Preparation Example 13 were placed on a heater in the chamber and fumigated. More than 90% of the mosquitos were knocked down within 20 minutes.

EXAMPLE 18

Among the dusts formulated according to Preparation Example 6, those containing the present compounds (2), (7), (12), (20), (25) and (32) were each dusted, using Belljar duster, on the rice plants in a 1/50,000 Wagner pot which had elapsed 45 days after sowing, in a proportion of 3 kg/10 are. After covering the pot with wire net, about 30 green rice leafhopper adults (*Nephotettix cincticeps*) were liberated therein. After one day, more than 70% of the test insects were killed.

EXAMPLE 19

Among the emulsifiable concentrates formulated according to Preparation Example 1, those containing the present compounds (1), (3), (4), (10), (14), (21), (28) and (33) were each diluted 500 times with water. Each test solution thus prepared was sprayed, by means of a turn table, on the rice plants in a 1/100,000 Wagner's pot which had been grown up to the tillering stage.

Thereafter, the eggs just before hatch of rice stem borer (*Chilo suppressalis*) were inoculated into the rice plants in a proportion of 100/pot. After four days, the death and alive of the insect in the rice plant were checked. As the results, the mortality was 100% with any emulsifiable concentrate.

EXAMPLE 20

Carmine mite female adults (*Tetranychus cinnabarinus*) were made parasitic on the leaves of potted kidney beans (2-leaf stage) which had elapsed 9 days after sowing, in a proportion of 10 - 15/leaf. After leaving them as they are for seven days, a numerous number of carmine mites were found to be bored at various growth stages. Among the emulsifiable concentrates formulated according to Preparation Example 1, those containing the present compounds (1), (4), (14), (19), (23), (30) and (33) were each diluted 500 times with water. At this time, each test solution thus prepared was sprayed in a proportion of 10 cc/pot by means of a turn table. After 10 days, damage of the kidney beans by the insects was checked. As the results, an increase in the damage was not observed with any emulsifiable concentrate.

EXAMPLE 21

A green-house (3 m in height) was divided into plots having an area of 30 m² and chinese cabbages were grown up therein. Thereafter, armyworms and cutworms, cabbage worm and diamond-back moth were artificially made parasitic on the cabbages. The present compounds (1), (3) and (4) were each dissolved in cellosolve to make a 20% solution. Each test solution thus prepared was sprayed under pressure on the cabbages so that the amount of the active ingredient becomes 50 g/10 are. Thus, no spread of damage by the insect was observed with any compound.

EXAMPLE 22

Ten liters of water were placed in a 14-liter polypropylene bucket, and 1 g of each of the granular preparations formulated according to Preparation Example 15 was added thereto. After one day, about 100 full grown northern house mosquito larvae (*Culex pipiens pallens*) were liberated in the water and the death and alive of the larvae were observed. As the results, more than 90% of the larvae were killed with 24 hours.

What is claimed is:

1. A compound of the formula,

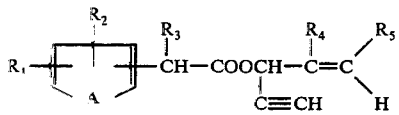

wherein $R_1$ and $R_2$ are each hydrogen or a halogen atom, a $C_1$-$C_4$ alkyl, $C_2$-$C_4$ alkenyl, nitro, $C_1$-$C_4$ alkanoyl, an $C_1$-$C_4$ alkanoyloxy, or $R_1$ and $R_2$, taken together, may form, a $C_3$-$C_5$ alkylene or butadienylene (—CH=•CH—CH=CH—) ring; $R_3$ is a $C_2$-$C_4$ alkyl, $C_2$-$C_4$ alkenyl, propargyl, cyclo $C_3$-$C_6$ alkyl or cyclopropylmethyl group; $R_4$ is hydrogen or a halogen atom, methyl or ethyl group; $R_5$ is allyl, propargyl, 3-butenyl, 3-butynyl, phenyl or benzyl group; and A is a —CH=CH— group.

2. The compound according to claim 1, wherein $R_1$ and $R_2$ are each hydrogen, fluorine, chlorine or bromine atom, a $C_1$-$C_4$ alkyl, $C_2$ alkenyl, nitro, acetyl, or acetyloxy, or $R_1$ and $R_2$, taken together, may form tri- or tetra-methylene ring or butadienylene ring; $R_3$ is a $C_2$-$C_4$ alkyl, $C_3$-$C_6$ cycloalkyl, cyclopropylmethyl, allyl or propargyl group; $R_4$ is hydrogen or chlorine atom, or a $C_1$-$C_2$ alkyl group.

3. The compound according to claim 2 wherein $R_1$ and $R_2$ are each hydrogen, fluorine, chlorine or bromine atom, a $C_1$-$C_4$ alkyl, $C_2$ alkenyl, nitro, acetyl, or acetyloxy or $R_1$ and $R_2$, taken together, may form a tri- or tetra-methylene ring;

4. The compound according to claim 3, which has the formula,

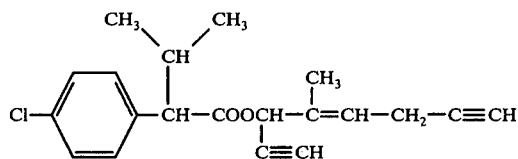

5. The compound according to claim 3, which has the formula,

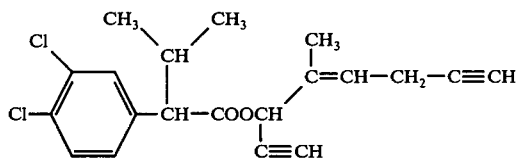

6. The compound according to claim 3, which has the formula,

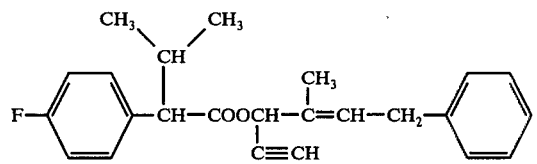

7. The compound according to claim 3, which has the formula,

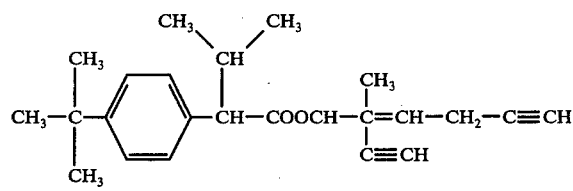

8. The compound according to claim 3, which has the formula,

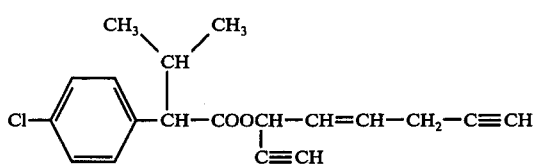

9. An insecticidal and/or acaricidal composition comprising an insecticidally or acaricidally effective amount of a compound according to claim 1 and an inert carrier.

10. A method for killing insects or acarids which comprises applying thereto an insecticidally and/or acaricidally effective amount of a compound according to claim 1.

* * * * *